US012588800B2

(12) United States Patent (10) Patent No.: US 12,588,800 B2
Matsuoka (45) Date of Patent: Mar. 31, 2026

(54) ENDOSCOPE TREATMENT TOOL

(71) Applicant: OLYMPUS CORPORATION, Tokyo (JP)

(72) Inventor: Yuya Matsuoka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 948 days.

(21) Appl. No.: 17/182,714

(22) Filed: Feb. 23, 2021

(65) Prior Publication Data

US 2021/0169309 A1 Jun. 10, 2021

Related U.S. Application Data

(63) Continuation of application No. PCT/JP2018/038953, filed on Oct. 19, 2018.

(51) Int. Cl.
*A61B 1/00* (2006.01)
*A61B 1/018* (2006.01)
(Continued)

(52) U.S. Cl.
CPC ...... *A61B 1/00098* (2013.01); *A61B 1/00135* (2013.01); *A61B 1/0014* (2013.01);
(Continued)

(58) Field of Classification Search
CPC ............ A61B 1/00098; A61B 1/00135; A61B 1/0014; A61B 1/018; A61B 17/29;
(Continued)

(56) References Cited

U.S. PATENT DOCUMENTS

2005/0234297 A1* 10/2005 Devierre ............ A61B 1/00087
600/129
2008/0249354 A1* 10/2008 Muyari .............. A61B 18/1492
600/104
(Continued)

FOREIGN PATENT DOCUMENTS

EP 1977708 A1 10/2008
JP 2007-532262 A 11/2007
(Continued)

OTHER PUBLICATIONS

International Search Report dated Jan. 8, 2019 issued in PCT/JP2018/038953.

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

Provided is an endoscope treatment tool including: a tubular distal-end member that is attached to the distal end of an endoscope; an outer sheath having a channel extending in a direction along a longitudinal axis of the endoscope; a treatment-tool body; a linear connector that connects the distal-end member and the treatment-tool body. The treatment-tool body includes a bendable long insertion portion that is inserted through the channel, a treatment portion with which treatment is performed, and a rotating member. The rotating member includes a through-hole that extends along a plane intersecting the longitudinal axis and through which the connector is inserted. When the treatment-tool body is pushed in the longitudinal direction, the connector guides the treatment portion along a locus centered on an axis intersecting a plane including the axis of the distal-end member and the axis of the channel.

13 Claims, 6 Drawing Sheets

(51) Int. Cl.
  *A61B 17/29*  (2006.01)
  *A61B 18/14*  (2006.01)

(52) U.S. Cl.
  CPC .............. *A61B 1/018* (2013.01); *A61B 17/29* (2013.01); *A61B 18/1492* (2013.01)

(58) Field of Classification Search
  CPC ............ A61B 18/1492; A61B 1/00087; A61B 1/00131; A61B 2017/00296; A61B 2017/2905; A61B 2017/2929
  USPC ........................................................ 600/106
  See application file for complete search history.

(56) References Cited

U.S. PATENT DOCUMENTS

| | | | |
|---|---|---|---|
| 2009/0259141 A1 | 10/2009 | Ewers et al. | |
| 2016/0029875 A1* | 2/2016 | Okada ................ | A61B 1/00101 600/107 |
| 2016/0338771 A1* | 11/2016 | Kobayashi ......... | A61B 18/1492 |

FOREIGN PATENT DOCUMENTS

| | | |
|---|---|---|
| JP | 2008-253597 A | 10/2008 |
| JP | 2010-022568 A | 2/2010 |
| JP | 2012-024597 A | 2/2012 |
| WO | WO 2006/033671 A2 | 3/2006 |
| WO | WO 2009/117696 A1 | 9/2009 |
| WO | WO 2014/199759 A1 | 12/2014 |

* cited by examiner

ENDOSCOPE TREATMENT TOOL

CROSS-REFERENCE TO RELATED APPLICATIONS

This is a continuation of International Application PCT/JP2018/038953, with an international filing date of Oct. 19, 2018, which is hereby incorporated by reference herein in its entirety.

TECHNICAL FIELD

The present invention relates to an endoscope treatment tool.

BACKGROUND ART

There is a known endoscope treatment tool that includes: a cap that is detachably attached to a distal end of an endoscope; a treatment tool that is provided so as to be able to be moved forward and backward in the longitudinal direction of the endoscope with respect to the cap and with which treatment is performed on living tissue; and a linear connecting member that connects the cap and the treatment tool (for example, see Japanese Translation of PCT International Application, Publication No. 2008-253597).

The cap has a channel provided on an outer circumferential surface of the cap so as to be parallel to the longitudinal axis. The treatment tool includes: an insertion portion that is inserted through the channel so as to be movable in the longitudinal direction; and a treatment portion that is provided at a distal end of the insertion portion and with which treatment is performed on living tissue.

The treatment portion has, at a proximal end thereof, a through-hole that penetrates therethrough in a direction perpendicular to the longitudinal direction of the insertion portion, and an intermediate section of the connecting member is inserted through the through-hole. Both ends of the connecting member bent in a C-shaped manner are rotatably fitted into coaxial holes provided at both sides of the cap. Accordingly, when the treatment tool is pushed forward, the connecting member is made to swivel about the holes provided in the cap and is rotated inside the through-hole, which is provided in the treatment tool, and the treatment portion is guided by the connecting member so as to move along an arc-shaped locus from a lateral position of the cap to a front position of the cap.

SUMMARY OF INVENTION

According to one aspect, the present invention provides an endoscope treatment tool including: a tubular distal-end member that is attached to a distal end of an endoscope; an outer sheath that has a channel extending in a direction along a longitudinal axis of the endoscope; a treatment-tool body a part of which is inserted into the channel and with which treatment is performed on living tissue; and a linear connecting member that connects the distal-end member and the treatment-tool body; wherein the treatment-tool body includes a bendable long insertion portion that is inserted through the channel so as to be movable in the direction along the longitudinal axis, a treatment portion that is disposed at a distal end of the insertion portion and with which treatment is performed on the living tissue, and a rotating member that is disposed at a proximal end of the treatment portion and that comprises a through-hole that extends along a plane intersecting the longitudinal axis of the insertion portion and through which the connecting member is inserted so as to be movable, and wherein, when the treatment-tool body is pushed in the longitudinal direction of the insertion portion, the connecting member guides the treatment portion along a locus centered on an axis intersecting a plane including the axis of the distal-end member and the axis of the channel.

DESCRIPTION OF EMBODIMENT

An endoscope treatment tool 1 according to one embodiment of the present invention will be described below with reference to the drawings.

Figure 1:
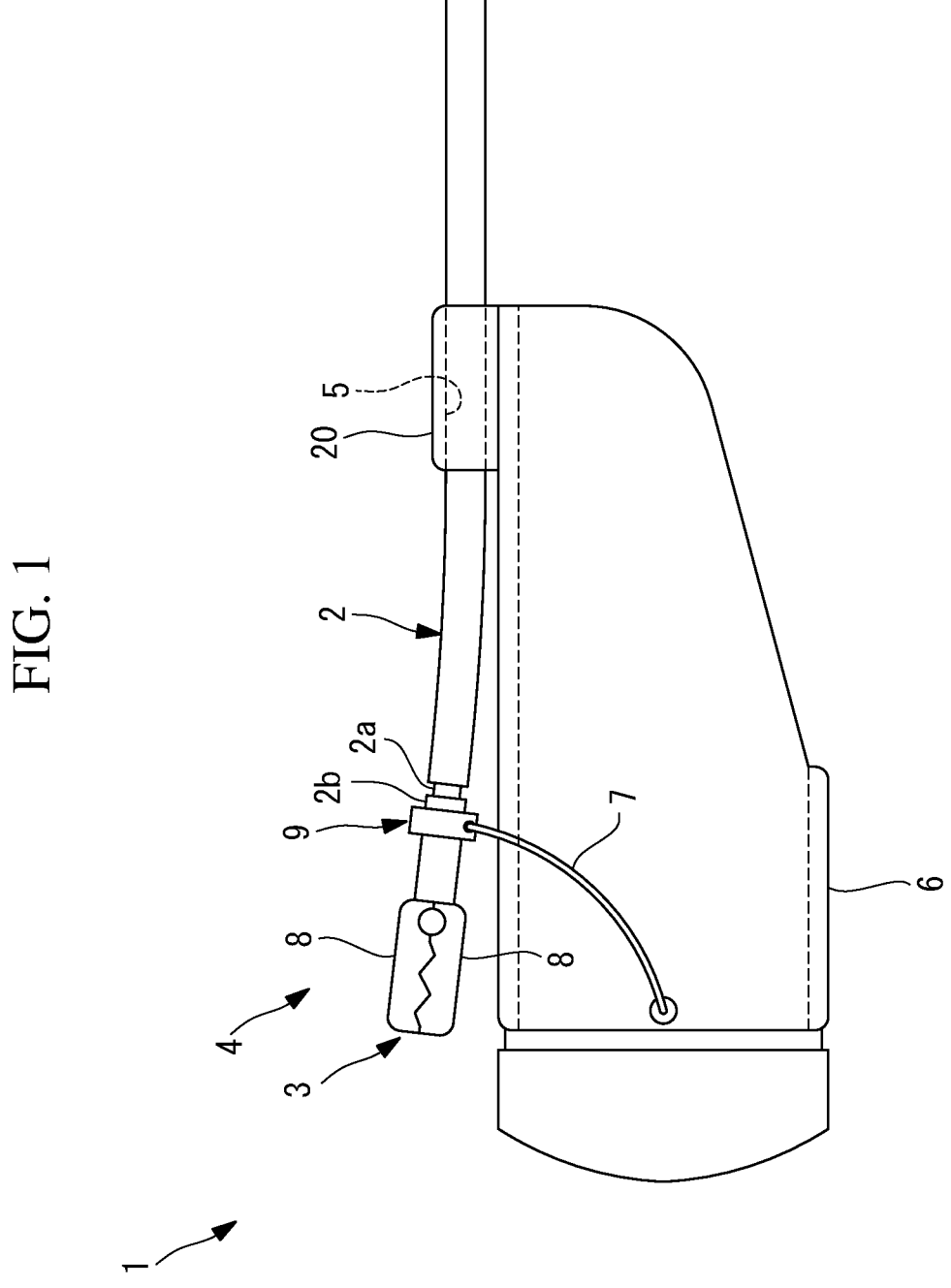
FIG. 1 is a side view showing a distal-end section of an endoscope treatment tool according to one embodiment of the present invention.

As shown in FIG. 1, the endoscope treatment tool 1 of this embodiment includes: a treatment-tool body 4 that includes a long flexible insertion portion 2 and a treatment portion 3 that is disposed at a distal end of the insertion portion 2; an outer sheath 20 that includes a channel 5 through which the insertion portion 2 of the treatment-tool body 4 is inserted so as to be movable in the longitudinal direction; a cap (distal-end member) 6 that is detachably attached to a distal end of an endoscope 100; and a connecting member (connector) 7 that connects the cap 6 and the treatment-tool body 4.

Figure 3:
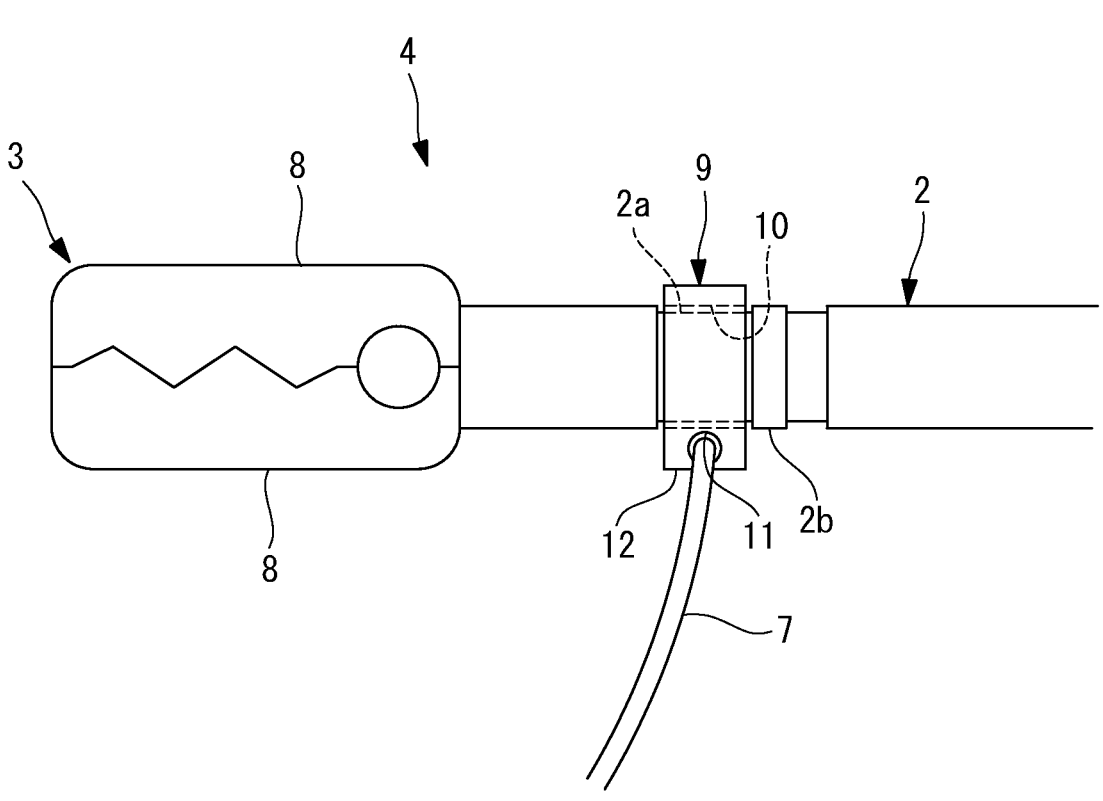
FIG. 3 is an enlarged view partially showing a treatment-tool body of the endoscope treatment tool shown in FIG. 1.

As shown in FIG. 3, the insertion portion 2 includes, at a region close to the distal end, a recessed section 2a an outer diameter dimension of which is less than an outer diameter dimension of the insertion portion 2 at the other region, and a stopper part 2b that is attached to the recessed section 2a. The stopper part 2b is a ring member that has an outer diameter dimension slightly larger than an inner diameter dimension of a first through-hole 10, to be described later, and can be fixed to the recessed section 2a.

The treatment portion 3 is, for example, gripping forceps for gripping living tissue, which is a treatment target, includes a pair of gripping pieces 8 capable of being opened and closed, and transmits a force applied at a proximal end of the insertion portion 2 to the gripping pieces 8 via a wire (not shown) inserted through the insertion portion 2, to open and close the gripping pieces 8.

A cylindrical rotating member 9 that is supported so as to be rotatable about a longitudinal axis of the insertion portion 2 is disposed at a proximal end of the treatment portion 3 of the treatment-tool body 4.

Figure 4:
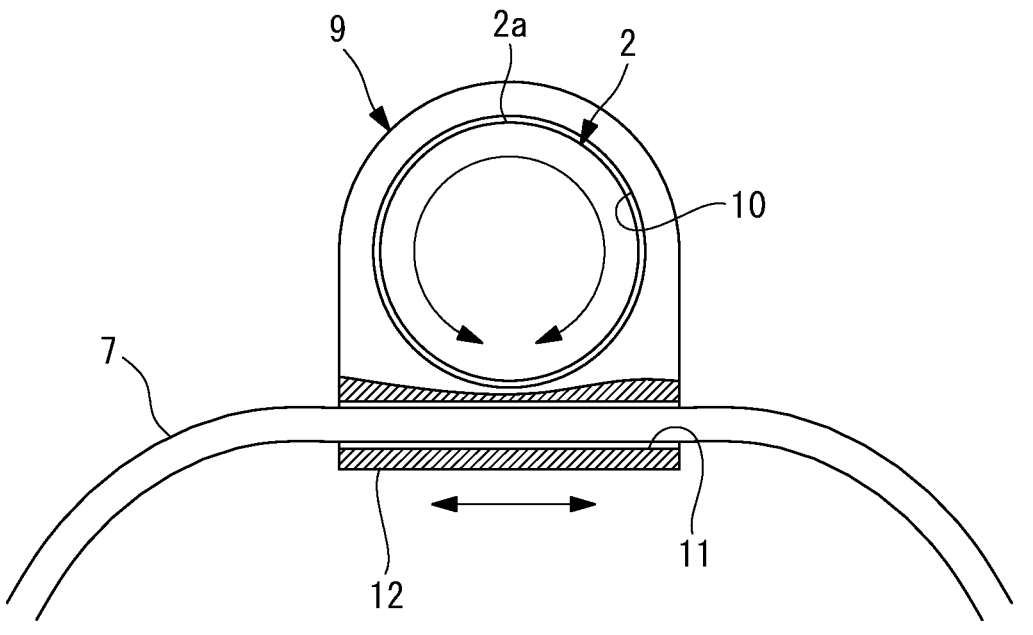
FIG. 4 is a front view partially showing, in cross section, a rotating member included in the treatment-tool body of the endoscope treatment tool shown in FIG. 1.

As shown in FIGS. 3 and 4, the rotating member 9 includes: the first through-hole 10, which is provided along the axial direction and which has an inner diameter dimension slightly larger than the outer diameter dimension of the recessed section 2a of the insertion portion 2; and a second through-hole (through-hole) 11 that is disposed so as to be in such a positional relationship that the first through-hole 10 and the second through-hole 11 serve as skew lines, and that penetrates the rotating member 9 in a radial direction along a plane perpendicular to the axis of the first through-hole 10. An outer surface of the rotating member 9 on the second through-hole 11 side is formed of a flat surface (flat-surface section) 12 parallel to the second through-hole 11. The flat surface 12 is brought into contact with an outer surface of the cap 6, thereby making it possible to more stabilize the orientation of the rotating member 9.

The insertion portion 2 is inserted through the first through-hole 10, and the rotating member 9 is disposed at the recessed section 2a of the insertion portion 2, whereby the rotating member 9 is supported so as to be rotatable about the longitudinal axis of the insertion portion 2 with respect to the insertion portion 2. After the rotating member 9 is disposed at the recessed section 2a of the insertion portion 2, the stopper part 2b is attached to a position of the recessed section 2a close to a proximal end of the rotating member 9, thereby restricting movement of the rotating member 9 in the axial direction with respect to the insertion portion 2.

Furthermore, the rotating member 9 is disposed at such a position that the outer surface thereof that is formed of the flat surface 12 is located on the cap 6 side. Accordingly, the connecting member 7, which is inserted through the second through-hole 11, is disposed at such a position as to pass between the treatment-tool body 4 and the cap 6.

The cap 6 is a transparent resin-made cylindrical member that covers the endoscope 100 in the axial direction from the distal end of the endoscope 100.

In FIG. 1, the outer sheath 20 is integrally provided on an outer circumferential surface of the cap 6 so as to be apart from the rotating member 9 toward the proximal end along the longitudinal axis of the insertion portion 2.

In the vicinity of a section of the outer circumferential surface of the cap 6, the section being located at an upper side of the field of view of the endoscope 100 when the cap 6 is mounted on the distal end of the endoscope 100, the channel 5 has an inner diameter dimension that allows the insertion portion 2 of the treatment-tool body 4 to be inserted so as to be movable in the longitudinal direction.

The connecting member 7 is a resin thread and is inserted through the second through-hole 11 of the rotating member 9. Both ends of the connecting member 7 are respectively fixed to right and left sections of the outer circumferential surface of the cap 6, the right and left sections being located at right and left sides of the field of view of the endoscope when the cap 6 is mounted on the distal end of the endoscope 100.

The operation of the thus-configured endoscope treatment tool 1 of this embodiment will be described below.

Figure 5:
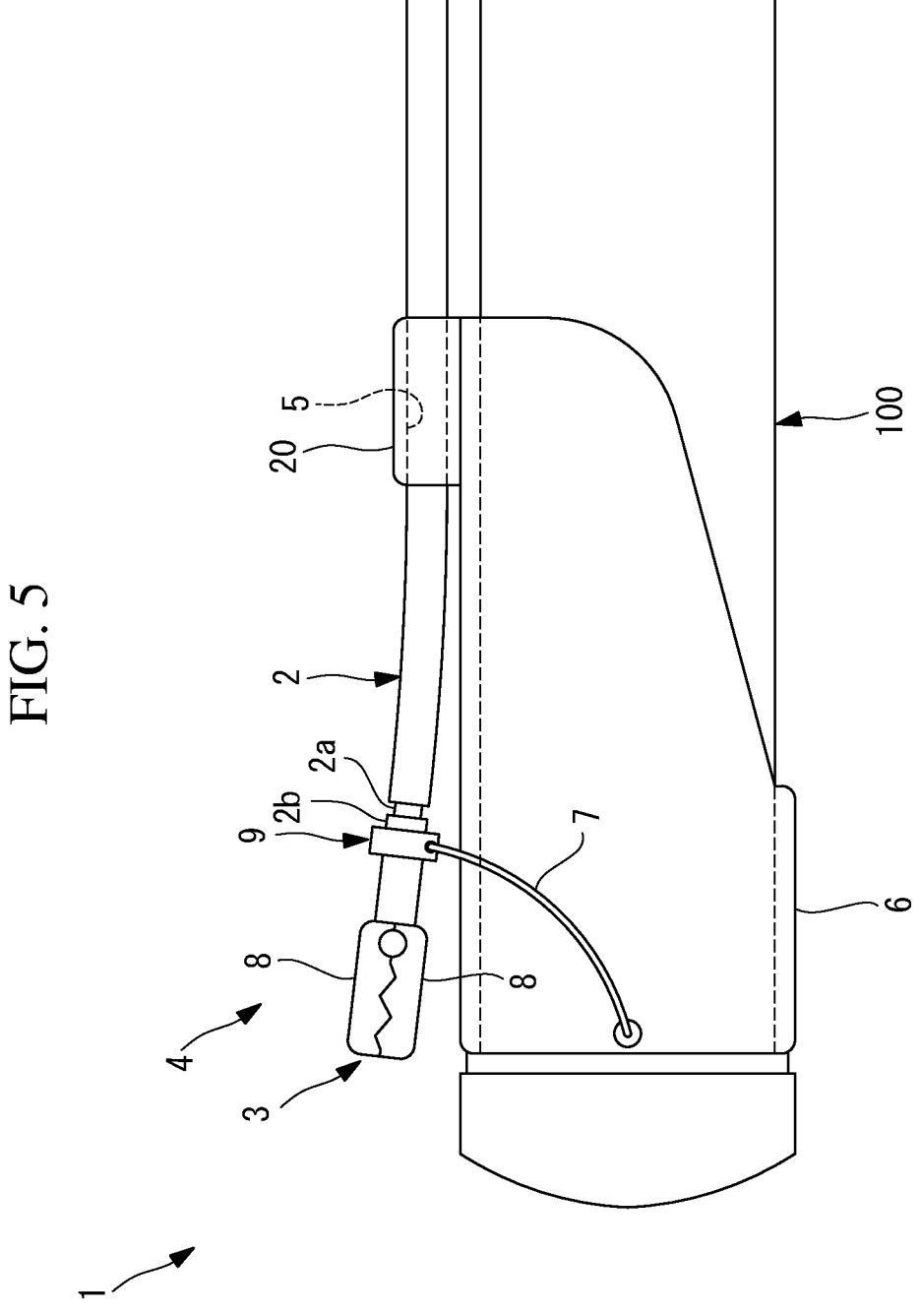
FIG. 5 is a side view showing a state in which the endoscope treatment tool shown in FIG. 1 has been mounted on a distal end of an endoscope.

In order to perform treatment, such as endoscopic submucosal dissection (ESD), by using the endoscope treatment tool 1 of this embodiment, first, as shown in FIG. 5, the endoscope treatment tool 1 is mounted on the endoscope 100 by mounting the cap 6 on the distal end of the endoscope 100. At this time, the endoscope treatment tool 1 is mounted at such an angle that the channel 5, through which the treatment-tool body 4 is inserted, is located at the upper side of the field of view of the endoscope 100.

Next, the endoscope 100 on which the endoscope treatment tool 1 has been mounted is inserted into a body cavity of a patient and is inserted until an affected area is located in the field of view of the endoscope 100. Then, the endoscope 100 is rotated about the longitudinal axis, thereby adjusting the angle of the endoscope 100 such that the affected area is located at a lower side of the field of view.

Figure 6:
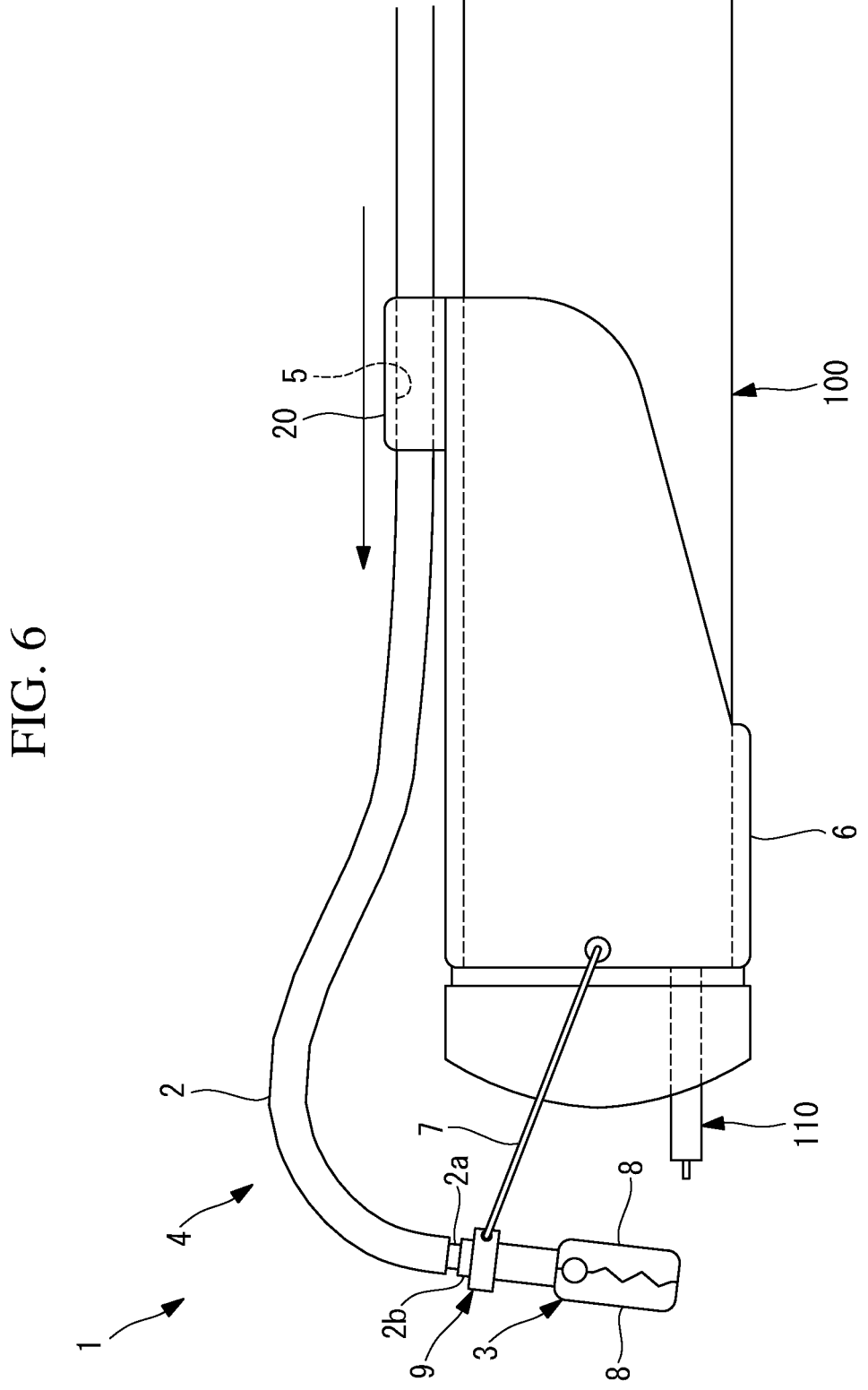
FIG. 6 is a side view showing a state in which the treatment-tool body of the endoscope treatment tool shown in FIG. 5 has been moved forward with respect to a cap.

In this state, the insertion portion 2 of the treatment-tool body 4 is pushed in such a direction as to be moved forward, whereby the treatment portion 3 is moved forward, as shown in FIG. 6. Because the rotating member 9, which is provided on the treatment-tool body 4, is restrained to the cap 6 by the connecting member 7, when the insertion portion 2 is kept to be pushed in the longitudinal direction in a state in which the connecting member 7 is extended without slack, while the insertion portion 2 is bent between the proximal end of the rotating member 9 and the distal end of the outer sheath 20, the treatment portion 3 is moved, to a position where the treatment portion 3 is put downward, along an arc-shaped locus by the connecting member 7.

At this position, the treatment portion 3 is opened and closed to grip living tissue of the affected area, and the insertion portion 2 is pulled backward, whereby the gripped living tissue can be raised. Then, a treatment tool 110, such as a high-frequency knife, guided through a channel (not shown) of the endoscope 100 is made to protrude from the distal end of the endoscope 100, and the raised living tissue can be incised.

In this case, because the connecting member 7, which is formed of a thread, is inserted through the second through-hole 11 of the rotating member 9, rotation of the treatment portion 3 about the axis of the second through-hole 11 is allowed, and the connecting member 7 and the rotating member 9 can be relatively moved in the direction along the axis of the second through-hole 11.

In particular, because the connecting member 7 is formed of a thread, for example, in a case in which there arises a need to change the field of view by moving the endoscope 100 with the living tissue being gripped by the treatment portion 3, the connecting member 7 is moved inside the second through-hole 11 or the connecting member 7, which is formed of a thread, is deformed, whereby the gripped state of the living tissue can be maintained without causing the treatment portion 3 to follow the movement of the endoscope 100.

Then, in this case, the rotating member 9 is rotated about the longitudinal axis of the treatment-tool body 4, whereby the second through-hole 11 and the connecting member 7, which is inserted through the second through-hole 11, are disposed in such a positional relationship as not to restrain each other. Accordingly, it is possible to suppress an increase in the friction therebetween and to allow free relative movement.

Because the rotating member 9 is attached so as to be rotatable about the longitudinal axis of the insertion portion 2, even when the insertion portion 2 is rotated inside the channel 5 of the outer sheath 20, it is possible to prevent the second through-hole 11, through which the connecting member 7 is inserted, from being rotated about the axis of the first through-hole 10. Accordingly, there is an advantage in that an increase in the resistance between the treatment-tool body 4 and the connecting member 7 is prevented, thereby making it possible to prevent restriction of the movement of the treatment-tool body 4 with respect to the connecting member 7.

Specifically, in a case in which a through-hole through which the connecting member 7 is inserted is provided in the treatment-tool body 4 as in the related art, when the treatment-tool body 4 is rotated about the longitudinal axis, there is a disadvantage in that the connecting member 7, which is formed of a thread, is wrapped around the treatment-tool body 4; however, according to this embodiment, because the connecting member 7 is not rotated even when the treatment-tool body 4 is rotated about the longitudinal axis, it is possible to prevent the connecting member 7 from being wrapped around the treatment-tool body 4. Specifically, twisting of the connecting member 7 can be prevented without impairing the swivel function of the treatment-tool body 4.

According to this embodiment, because the second through-hole 11, through which the connecting member 7 is inserted, is disposed at a position between the treatment-tool body 4 and the cap 6, there is an advantage in that it is possible to always dispose the treatment-tool body 4 radially outside the connecting member 7 and to prevent a situation in which the movement of the treatment-tool body 4 is disturbed by the connecting member 7.

In this embodiment, although a resin thread that is a flexible linear member is adopted as the connecting member 7, instead of this, a relatively rigid wire may be adopted. In this case, a situation in which the wire is tilted inside the second through-hole 11 and is strongly pressed against an inner surface of the second through-hole 11 is prevented by rotating the rotating member 9 about the longitudinal axis of the treatment-tool body 4. Accordingly, there is an advantage in that smooth relative movement of the second through-hole 11 and the wire can be allowed.

Figure 7:
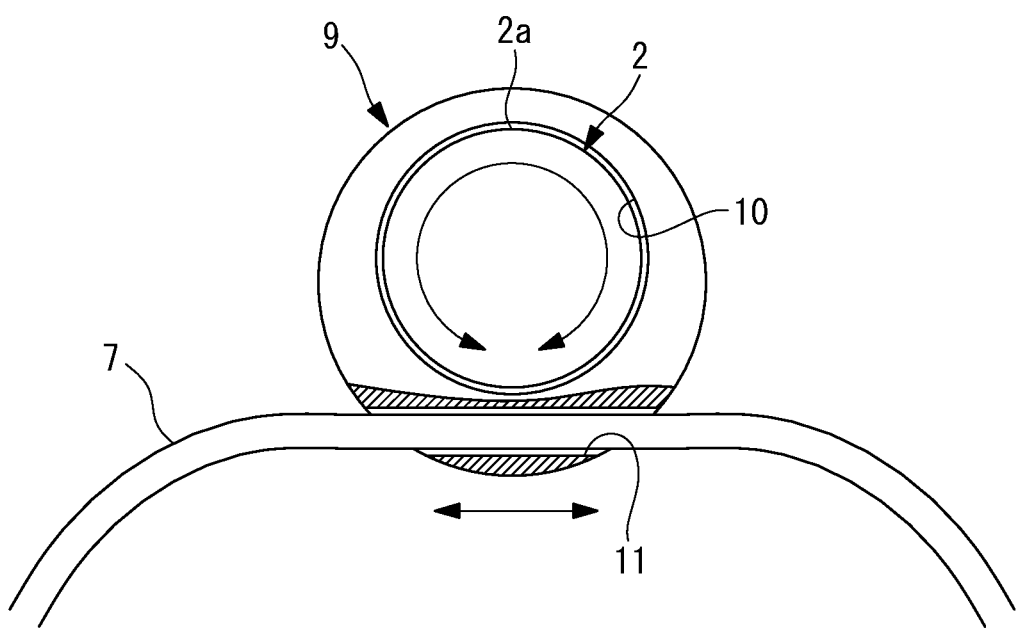
FIG. 7 is a front view partially showing, in cross section, a modification of the rotating member shown in FIG. 4.

In this embodiment, although the rotating member 9 includes the outer surface that is formed of the flat surface 12, instead of this, as shown in FIG. 7, the rotating member 9 may be formed in a ring shape having, as an outer surface, a cylindrical surface over the entire circumference.

Although a cylindrical member has been illustrated as the cap 6, the outer-surface shape thereof is not limited to a cylinder shape, and a cap having another arbitrary cylinder shape may be adopted.

Figure 2:
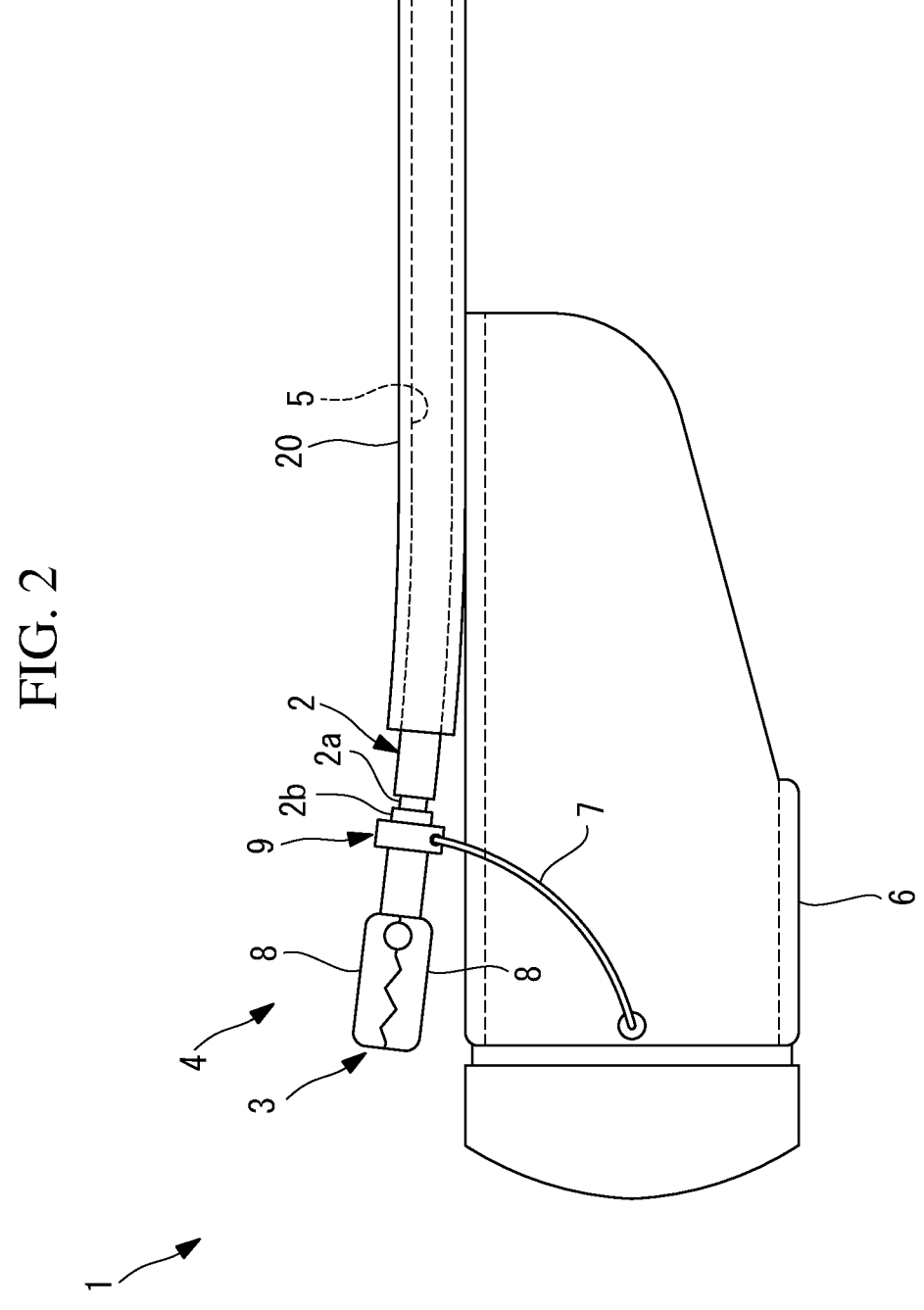
FIG. 2 is a side view showing a modification of the endoscope treatment tool shown in FIG. 1.

In this embodiment, the outer sheath 20, which is integrally provided on the outer circumferential surface of the cap 6, has been illustrated, instead of this, as shown in FIG. 2, it is also possible to adopt a separate or detachable outer sheath.

In this case, the outer sheath 20 is an outer sheath that is separate from the cap 6 and that is freely movable. Then, the channel 5 in the outer sheath 20 is hollow so as to extend along the cap 6.

In this embodiment, although the stopper part 2b of the insertion portion 2, which is detachably attached to the recessed section 2a of the insertion portion 2, has been illustrated, instead of this, it is also possible to adopt a structure in which a step is integrally formed on the insertion portion 2. In this case, the step is formed in the recessed section 2a at a position away from the position where the outer diameter dimension of the insertion portion 2 changes, by a slightly larger distance than the width dimension of the rotating member 9, in the direction along the longitudinal axis.

As a result, the following aspect is read from the above-described embodiment of the present invention.

According to one aspect, the present invention provides an endoscope treatment tool including: a tubular distal-end member that is attached to a distal end of an endoscope; an outer sheath that has a channel extending in a direction along a longitudinal axis of the endoscope; a treatment-tool body a part of which is inserted into the channel and with which treatment is performed on living tissue; and a linear connecting member that connects the distal-end member and the treatment-tool body; wherein the treatment-tool body includes a bendable long insertion portion that is inserted through the channel so as to be movable in the direction along the longitudinal axis, a treatment portion that is disposed at a distal end of the insertion portion and with which treatment is performed on the living tissue, and a rotating member that is disposed at a proximal end of the treatment portion and that comprises a through-hole that extends along a plane intersecting the longitudinal axis of the insertion portion and through which the connecting member is inserted so as to be movable, and wherein, when the treatment-tool body is pushed in the longitudinal direction of the insertion portion, the connecting member guides the treatment portion along a locus centered on an axis intersecting a plane including the axis of the distal-end member and the axis of the channel.

According to this aspect, when the insertion portion of the treatment-tool body, which has been inserted through the channel of the distal-end member mounted on the distal end of the endoscope, is moved forward and backward in the longitudinal direction of the insertion portion, the treatment portion is guided along the arc-shaped locus by the linear connecting member. Because the connecting member is inserted through the through-hole of the rotating member, which is provided on the treatment-tool body, rotation of the treatment portion about the axis of the through-hole is allowed, and the connecting member and the rotating member can be relatively moved in the direction along the axis of the through-hole.

In this case, because the rotating member is attached so as to be rotatable about the longitudinal axis of the insertion portion, even when the insertion portion is rotated inside the channel of the distal-end member, it is possible to prevent rotation of the through-hole through which the connecting member is inserted. Accordingly, it is possible to prevent an increase in the resistance between the treatment-tool body and the connecting member and to prevent restriction of movement of the treatment-tool body with respect to the connecting member. Furthermore, twisting of the connecting member can be prevented without impairing the swivel function of the treatment-tool body.

In the above-described aspect, the insertion portion may be disposed, between a proximal end of the rotating member and the outer sheath, away from a distal end of the outer sheath along the longitudinal axis of the insertion portion.

In the above-described aspect, the connecting member may be a flexible linear member.

With this configuration, when a gripping portion is moved in the direction of the axis of the through-hole, the connecting member, which is formed of the flexible linear member, is deformed, thus making the movement easier. In this case, even when the insertion portion is rotated inside the channel of the distal-end member, the connecting member, which is formed of the flexible linear member, can be prevented from being got entangled in the insertion portion.

In the above-described aspect, the linear member may be a thread made of resin.

In the above-described aspect, the through-hole may be disposed between the distal-end member and the insertion portion.

With this configuration, it is possible to dispose the treatment-tool body radially outside the connecting member and to prevent a situation in which movement of the treatment-tool body is disturbed by the connecting member.

In the above-described aspect, the rotating member may have, at a region of an outer circumferential surface, a flat-surface section that extends parallel to an axis of the through-hole and the longitudinal axis of the insertion portion.

With this configuration, the flat-surface section is just brought into contact with the outer circumferential surface of the distal-end member, whereby the rotating member can be prevented from being rotated about the longitudinal axis of the insertion portion.

REFERENCE SIGNS LIST 1 endoscope treatment tool
2 insertion portion
3 treatment portion
4 treatment-tool body
5 channel
6 cap (distal-end member)
7 connecting member (connector)
9 rotating member
11 second through-hole (through-hole)
12 flat surface (flat-surface section)
20 outer sheath
100 endoscope

The invention claimed is:

1. An endoscope treatment tool comprising:
a tubular distal-end member configured to be attached to a distal end of an endoscope;
a rotating member comprising:
a first through-hole extending along a direction of a longitudinal axis of the distal-end member, and
a second through-hole extending along an axis perpendicular to an axis of the first through-hole,
a linear connector connecting the distal-end member and the rotating member; and
a treatment-tool body inserted into and rotatably held by the first through-hole, a part of the treatment-tool body being configured to perform treatment on living tissue,
wherein the rotating member is configured to move in a direction along the axis of the second through-hole relative to the linear connector inserted in the second through hole,
the treatment-tool body includes a first portion and a second portion, the second portion located distally relative to the first portion, a diameter of the first portion being smaller than a diameter of the first through-hole, a diameter of the second portion being larger than the diameter of the first through-hole, and
a distal end of the rotating member is configured to abut a proximal end of the second portion.

2. The endoscope treatment tool according to claim 1, wherein the linear connector is a flexible linear member.

3. The endoscope treatment tool according to claim 2, wherein the linear member is a thread made of resin.

4. The endoscope treatment tool according to claim 1, wherein the second through-hole is disposed between the distal-end member and an insertion portion of the treatment-tool body.

5. The endoscope treatment tool according to claim 4, wherein the rotating member has, at a region of an outer circumferential surface, a flat-surface section that extends parallel to an axis of the second through-hole and a longitudinal axis of the insertion portion.

6. The endoscope treatment tool according to claim 1, further comprising an outer sheath fixed to the distal-end member, the outer sheath having a channel extending in a direction along a longitudinal axis of the endoscope,
wherein an insertion portion of the treatment-tool body is disposed, between a proximal end of the rotating member and the outer sheath, away from a distal end of the outer sheath along a longitudinal axis of the insertion portion.

7. The endoscope treatment tool according to claim 1, wherein, when the treatment-tool body is extended in the longitudinal direction of the insertion portion, the linear connector is configured to guide the treatment portion along a locus centered on an axis intersecting a plane including an axis of the distal-end member and an axis of the channel.

8. The endoscope treatment tool according to claim 1, wherein the treatment-tool body includes a third portion located proximally relative to the first portion, a diameter of the third portion being larger than the diameter of the first through-hole, and
wherein a proximal end of the rotating member is configured to abut a distal end of the third portion.

9. The endoscope treatment tool according to claim 1, wherein the rotating member is configured to move between the second portion and the third portion in the direction of the longitudinal axis.

10. The endoscope treatment tool according to claim 1, wherein the distal-end member having a channel arranged proximally relative to the rotating member, the channel accommodating a portion of the treatment tool body proximal to the first portion.

11. The endoscope treatment tool according to claim 10, wherein the channel is provided on a protrusion extending from an outer circumferential surface of the distal-end member.

12. The endoscope treatment tool according to claim 1, wherein the first through-hole having a first center axis extending in a longitudinal axis direction, the rotating member having a circular cross-section with a second center axis extending in the longitudinal axis direction, the first center axis being offset in a first direction from the second center axis in a radial direction perpendicular to the longitudinal axis direction.

13. The endoscope treatment tool according to claim 12, wherein a third center axis of the second through-hole extending perpendicular to the longitudinal axis, the third center axis of the second through-hole being offset in a second direction, opposite to the first direction, from the second center axis in the radial direction.

* * * * *